United States Patent
DeKeuster et al.

(10) Patent No.: US 10,285,864 B2
(45) Date of Patent: May 14, 2019

(54) AUTO-DARKENING WELDING HELMET

(71) Applicant: Snap-on Incorporated, Kenosha, WI (US)

(72) Inventors: Michael T DeKeuster, Mount Pleasant, WI (US); Roxanne M Stowell, Pleasant Prarie, WI (US)

(73) Assignee: Snap-on Incorporated, Kenosha, WI (US)

( * ) Notice: Subject to any disclaimer, the term of this patent is extended or adjusted under 35 U.S.C. 154(b) by 335 days.

(21) Appl. No.: 14/340,859

(22) Filed: Jul. 25, 2014

(65) Prior Publication Data

US 2016/0022496 A1    Jan. 28, 2016

(51) Int. Cl.
| | | |
|---|---|---|
| B23K 9/32 | (2006.01) | |
| A61F 9/06 | (2006.01) | |
| G02F 1/133 | (2006.01) | |

(52) U.S. Cl.
CPC .......... *A61F 9/067* (2013.01); *G02F 1/13306* (2013.01)

(58) Field of Classification Search
CPC ....... B23K 9/1087; B23K 9/321; B23K 9/322
USPC .................. 219/132, 147, 130.01; 2/8.2, 8.8
See application file for complete search history.

(56) References Cited

U.S. PATENT DOCUMENTS

| | | | |
|---|---|---|---|
| 1,717,538 A * | 6/1929 | Anderson | A47J 45/063 215/305 |
| 4,408,346 A | 10/1983 | Bauer | |
| 4,863,244 A | 9/1989 | Fuerthbauer | |
| 5,315,099 A | 5/1994 | Gunz et al. | |
| D393,933 S | 4/1998 | Huh | |
| 5,965,878 A * | 10/1999 | Vircks | G01D 5/34 250/214 PR |
| 6,067,129 A | 5/2000 | Fergason | |
| 6,242,711 B1 | 6/2001 | Cooper | |
| D446,887 S | 8/2001 | Young | |
| 6,614,409 B1 | 9/2003 | Bae | |

(Continued)

FOREIGN PATENT DOCUMENTS

| | | |
|---|---|---|
| CN | 100411598 A | 8/2008 |
| CN | 101623225 A | 1/2010 |

(Continued)

OTHER PUBLICATIONS

United Kingdom Intellectual Property Office Combined Search and Examination Report under Sections 17 and 18(3), dated Oct. 15, 2015; 7 pages.

(Continued)

*Primary Examiner* — Michael A Laflame, Jr.
(74) *Attorney, Agent, or Firm* — Seyfarth Shaw LLP (57) ABSTRACT

An auto-darkening eye protection apparatus such as a welding helmet includes an externally located combined push button and rotary switch coupled to lens control circuitry. A lens control setting display is configured on an internal portion of the apparatus and located in a field of view of a user when the lens is in a lowered operational position. The externally located combined push button and rotary switch is operable to select and adjust lens control parameters by a user wearing bulky hand protection such as welding gloves or welding mittens. The selection and adjustment level of the lens control parameters can be monitored on the display during the adjustment by a user while the lens is in the lowered operational position.

9 Claims, 6 Drawing Sheets

(56) References Cited

U.S. PATENT DOCUMENTS

| | | |
|---|---|---|
| D481,832 S | 11/2003 | Huh |
| D482,502 S | 11/2003 | Huh |
| D482,503 S | 11/2003 | Huh |
| 6,710,298 B2 | 3/2004 | Eriksson |
| 6,734,393 B1 | 5/2004 | Friedl et al. |
| 6,941,577 B2 | 9/2005 | Ackermann |
| D521,190 S | 5/2006 | Wu |
| 7,342,210 B2 | 3/2008 | Fergason |
| 7,462,806 B2 | 12/2008 | Huh |
| 7,926,118 B2 | 4/2011 | Becker et al. |
| 8,049,151 B2 * | 11/2011 | Huh .................. A61F 9/06 2/8.2 |
| 8,089,424 B2 | 1/2012 | Huh |
| 8,119,974 B2 | 2/2012 | Hamilton et al. |
| 8,217,742 B2 | 7/2012 | Trudeau et al. |
| 8,248,324 B2 * | 8/2012 | Nangle ............... G09B 19/24 2/8.2 |
| 8,316,462 B2 | 11/2012 | Becker et al. |
| 8,331,001 B2 | 12/2012 | Hsieh et al. |
| 8,457,949 B2 | 6/2013 | Huh |
| 8,569,655 B2 | 10/2013 | Cole |
| 8,659,509 B2 | 2/2014 | Huh |
| 2005/0017115 A1 | 1/2005 | Fergason |
| 2005/0017152 A1 | 1/2005 | Fergason |
| 2007/0056073 A1 | 3/2007 | Martin et al. |
| 2008/0082179 A1 | 4/2008 | Yang |
| 2008/0158502 A1 | 7/2008 | Becker et al. |
| 2009/0094721 A1 | 4/2009 | Becker |
| 2009/0298024 A1 * | 12/2009 | Batzler .............. B23K 9/32 434/234 |
| 2010/0108654 A1 * | 5/2010 | Ulrich .............. B23K 9/0953 219/130.5 |
| 2010/0140241 A1 | 6/2010 | Martin et al. |
| 2011/0010815 A1 | 1/2011 | Huh |
| 2011/0083241 A1 | 4/2011 | Cole |
| 2011/0316516 A1 | 12/2011 | Schiefermuller |
| 2013/0340141 A1 | 12/2013 | Huh |
| 2014/0013478 A1 | 1/2014 | Cole |

FOREIGN PATENT DOCUMENTS

| | | |
|---|---|---|
| CN | 102579189 A | 7/2012 |
| CN | 102741772 A | 10/2012 |
| CN | 204379541 | 6/2015 |
| EP | 2275061 A1 | 1/2011 |
| JP | 2001-174763 A | 6/2001 |

OTHER PUBLICATIONS

Canadian Intellectual Property Office Examiner's Report, dated Mar. 3, 2016; 6 pages.
Australian Government, Patent Examination Report No. 1, dated Sep. 29, 2015; 5 pages.
Canadian Intellectual Property Office Examiner's Report dated Apr. 4, 2017; 4 pages.
State Intellectual Property Office of P.R. China The First Office Action, dated Dec. 23, 2016; 8 pages.
Taiwan Office Action, dated Nov. 11, 2016; 13 pages.
Chinese Office Action for Application No. 201510146937.4 dated Mar. 20, 2018, 6 pages.
English version of the Chinese Office Action for Application No. 201510146937.4 dated Mar. 20, 2018, 3 pages.
Chinese Office Action for Application No. 201510146937.4 dated Aug. 21, 2017, 5 pages.
English version of the Chinese Office Action for Application No. 201510146937.4 dated Aug. 21, 2017, 3 pages.

* cited by examiner

AUTO-DARKENING WELDING HELMET

TECHNICAL FIELD OF THE INVENTION

The present application relates to an auto-darkening welding helmet and more particularly to an intuitive control system for adjusting multiple control parameters of an auto-darkening lens during use of an auto-darkening welding helmet.

BACKGROUND OF THE INVENTION

Welding helmets protect a user's eyes and skin from sparks and from potentially vision-damaging ultraviolet and infrared rays. Traditional welding helmets include a fixed shade with a glass lens, which remains darkened at all times. However, traditional welding helmets can be difficult to use because a user may need to frequently lift the helmet to examine a weldment welding joint and/or other work piece and set his position to prepare for welding and then lower the helmet again to perform the weld. This repetitive movement can case neck strain and may quickly fatigue a user.

More advanced auto-darkening helmets include variable controls that adjust the shade of a protective lens by incorporating quick-changing liquid crystal display LCD elements in the protective lens. Auto-darkening helmets include one or more light sensors and are configured to quickly darken to a pre-selected shade. Because a user can see clearly while the helmet is in a lowered position, auto-darkening helmets allow users to examine and set-up a weld in a weldment joint without raising the helmet. This increases a user's comfort and productivity by reducing fatiguing helmet adjustments and allowing more continuous work.

Currently available auto-darkening welding helmets are configured with adjustable settings for toggling between shade ranges. This allows users to adjust the shade of a protective lens based on a particular application. For example, higher shade levels may be appropriate for welding thick materials at high current settings or welding processes such as tungsten inert gas (TIG). On the other hand, lower shade levels may be more appropriate for lower current welding such as metal inert gas (MIG) welding or plasma arc or oxygen acetylene torch cutting to assure adequate visibility of the work piece to control the arc and judge appropriate travel speed.

Currently available auto-darkening welding helmets may also be configured with adjustable delay controls to lengthen or shorten the amount of time it takes for the helmet to return to a particular shade level following the completion of a weld. A relatively short delay setting of about 0.5 seconds may be appropriate to allow a user to move quickly between welds when a weld duration is short, for example, during a tack welding operation. A relatively long delay setting of about two seconds may be more appropriate for performing lengthy welds on thick materials so that the high shade level can be maintained to protect a user from viewing a larger, hotter weld until it has cooled.

Currently available auto-darkening welding helmets may also be configured with an adjustable sensitivity function to adjust the lens switching trigger from light to dark based on the ambient light conditions of the welding environment. For example, when welding outside, it is more appropriate to adjust to a higher setting in order for the lens to sense the arc starting. When welding in a darker area it is more appropriate to lower the sensitivity adjustment to minimize external light sources from inadvertently triggering the lens.

Some currently available auto-darkening welding helmets may include a combination of control input devices such as knobs, dials and push buttons to make adjustments to shade, delay and sensitivity, for example. Available auto-darkening helmets may include either external or internal controls. External controls allow some adjustments to be made while a helmet is being worn by a user. However, currently available helmets do not allow a user to view an indication of the control level being adjusted by an external control while the user wears the helmet in a lowered, operational state. Thus, the user is not provided with feedback to indicate the adjustment level while the helmet is in the lowered adjustment state or a direct indication of what each of the control knobs are as they are not within the user's line of sight. Moreover, some welding helmets with external controls are difficult or impossible to operate by a user wearing bulky user's gloves.

Some available auto-darkening welding helmets include internal controls positioned inside of the helmet that may only be accessed by removing the helmet. Such helmets generally cannot be adjusted while the helmet is being used for a welding operation. Other previously known auto-darkening helmets include internal controls that may be reachable when the helmet is in the lowered operational state but do not allow a user to view an indication of the control level being adjusted while the helmet is in the lowered, operational state for performing a welding operation. The user must estimate an adjustment state based on tactile feel of the control inputs and observed control effect on the lens. Moreover, internal adjustment controls that are reachable from the outside have been too small for practical manipulation by a worker wearing welding gloves. Thus each of the previously known auto-darkening welding helmets require a user to remove the helmet, raise the lens and/or remove welding gloves in order to accurately adjust the control settings.

SUMMARY OF THE INVENTION

According to aspects of the present disclosure, an auto-darkening welding helmet includes a multi-function knob located on the outside of the helmet that controls multiple adjustment parameters of an auto-darkening lens on the welding helmet. Setting levels of the adjustment parameters are indicated on heads up display located inside the welding helmet.

An auto-darkening helmet with a single knob located on the outside of the helmet is configured to allow a user to cycle between a number of adjustment modes and adjust corresponding setting for each selected mode without removing the helmet or raising the auto-darkening lens. The multi-function knob is coupled to control circuitry including a heads up display located inside of the helmet. The knob can be pushed inwardly to actuate a push button functionality of the multi-function knob that causes the control circuitry to cycle between different adjustment modes to select control parameters of the auto-darkening lens and enable adjustment of the selected parameter.

The multi-function knob can be rotated to adjust the settings of a selected mode once the desired parameter is reached (e.g., to control the amount of shade or the amount of delay time). The single knob is simpler than the multiple button controls of other welding helmets, which are also difficult to use with welding gloves, and the knob is located on the outside of the helmet so the user can reach it and control the relevant settings with the helmet on, unlike conventional welding helmets having internal controls that require the helmet to be removed.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

It should be understood that the comments included in the notes as well as the materials, dimensions and tolerances discussed therein are simply proposals such that one skilled in the art would be able to modify the proposals within the scope of the present disclosure.

DETAILED DESCRIPTION OF THE EMBODIMENTS

While aspects of the present disclosure include embodiments in many different forms, there is shown in the drawings, and will herein be described in detail, a preferred embodiment of the invention with the understanding that the present application is to be considered as an exemplification of the principles of the disclosure and is not intended to limit the broad aspect of the disclosure to embodiments illustrated.

According to an aspect of the present disclosure, an auto-darkening eye protection apparatus such as a welding helmet or welding visor includes a wearable lens retaining structure including an external surface and an internal surface. An adjustable auto-darkening light filtering lens is coupled to the wearable lens retaining structure. Lens control circuitry is coupled to the wearable lens retaining structure and to the lens. A combined push button and rotary switch is coupled to the lens control circuitry. The combined push button and rotary switch includes a knob portion extending outwardly away from the external surface of the wearable lens retaining structure. A lens control setting display is configured on the internal surface of the wearable lens retaining structure and coupled to the lens control circuitry. According to aspects of the present disclosure, the display is located in a field of view of a user when the lens is in a lowered operational position. The externally located combined push button and rotary switch is operable by a user while wearing the eye protection apparatus for selecting and adjusting lens control parameters. The switch is sized to facilitate manipulation by a user wearing bulky hand protection such as welding gloves or welding mittens.

Figure 1:
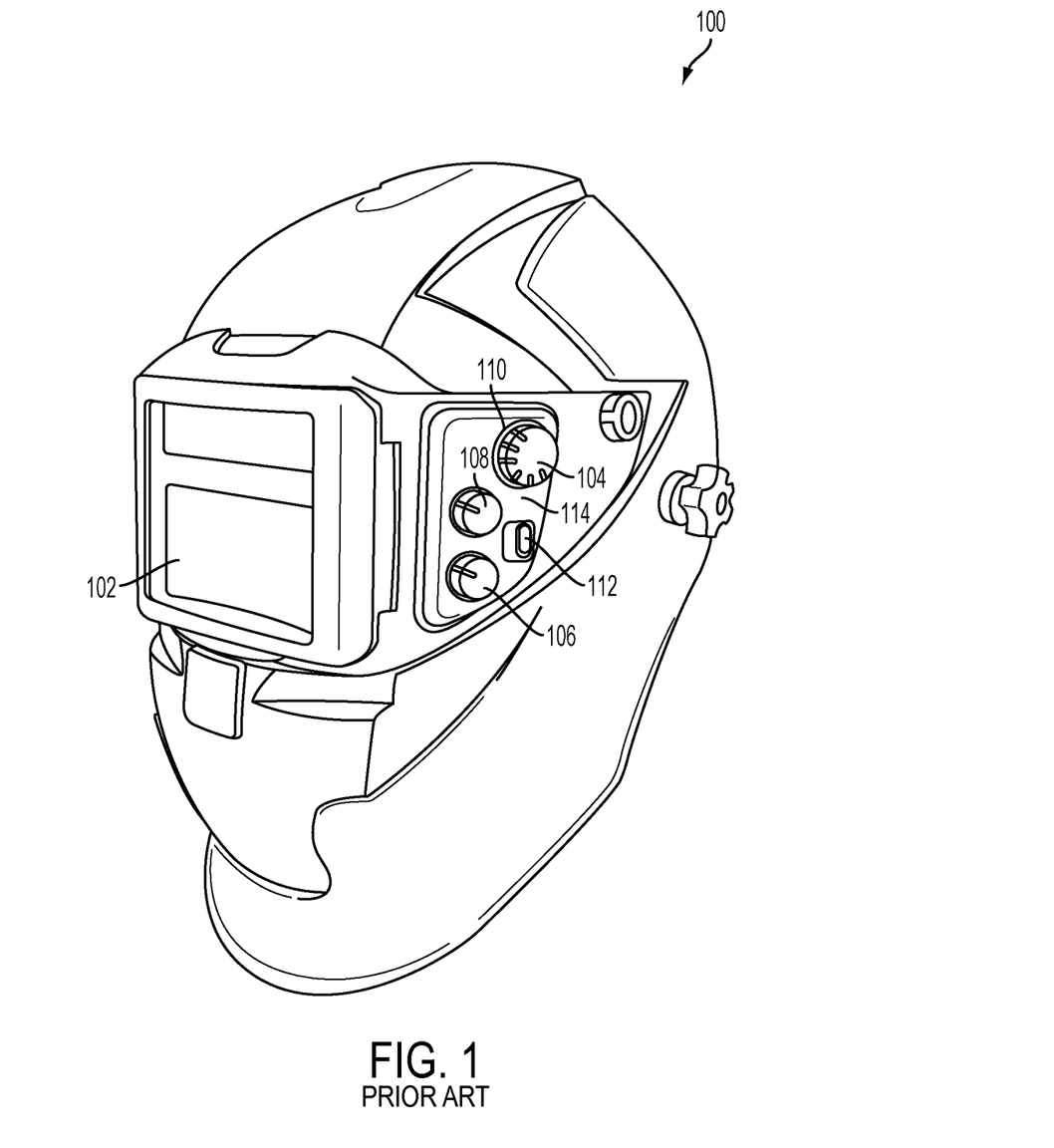
FIG. 1 is an illustration of a conventional auto-darkening welding helmet with external controls.

Referring to FIG. 1, an example of a conventional auto-darkening welding helmet 100 includes an auto-darkening lens 102 that protects a user from sparks and harmful ultraviolet and infrared light during welding. The helmet 100 includes a first externally mounted rotary adjustment knob 104 for controlling the shade level of the lens 102, a second externally mounted rotary adjustment knob 108 for controlling the delay time of the auto-darkening function of the lens 102, and a third external rotary adjustment knob 106 for controlling sensitivity of the auto-darkening lens 102. The helmet 100 also includes an externally mounted toggle switch 112 for selecting an operational mode of the auto-darkening lens. Adjustment setting markings 110 and knob identification markings 114 are displayed adjacent to the corresponding adjustment knobs 104, 106, 108 and switch 112.

The external toggle switch 112 and rotary adjustment knobs 104, 106, 108 are located within reach of a user such that the a user may make adjustments while wearing the helmet and while the lens 102 is in a lowered operational position. However, because a user cannot see the adjustment setting markings 110 or knob identification markings 112 while wearing the helmet the user may be unable to accurately determine the level control adjustment or identify a knob or switch without removing the helmet. Moreover, because the multiple adjustment knobs 104, 106, 108 are located in close proximity to each other, a user wearing bulky welding gloves may not be able to adjust a knob without interfering with the setting of an adjacent knob.

Figure 2:
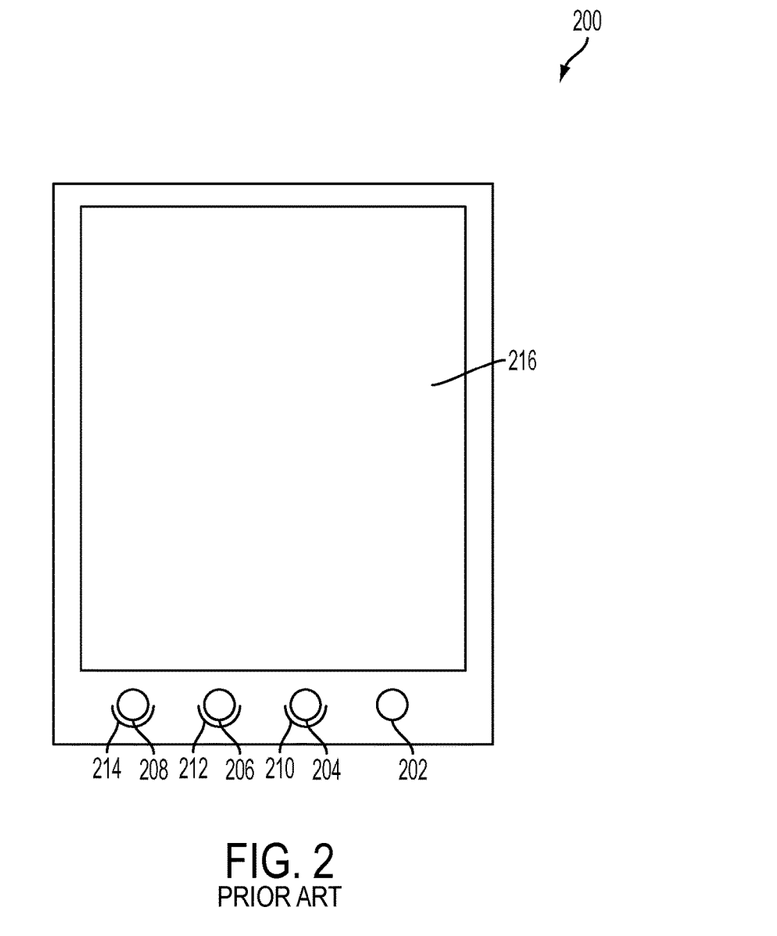
FIG. 2 is an illustration of a conventional internal control apparatus for an auto-darkening welding helmet.

Referring to FIG. 2, an example of conventional internal controls 200 for an auto-darkening welding helmet. In this example, an auto-darkening lens 216 is controlled by three rotary knobs 204, 206, 208 and a button 202. Adjustment setting markings 210, 212, 214 and knob identification markings are displayed adjacent to the corresponding adjustment knobs 204, 206, 208 and on the button 202. In this example, the internal controls 200 are generally unsuitable for adjusting while a user is wearing the helmet and while the lens 216 is in a lowered operational state because the internally mounted knobs 204, 206, 208 and button 202 may be difficult or impossible to reach without removing the helmet or raising the lens. Moreover, the relatively small size of the internally mounted knobs 204, 206, 208 and button 202 may not permit manipulation by a user wearing bulky welding gloves, even when the helmet is removed and/or when the lens is raised.

Figure 3:
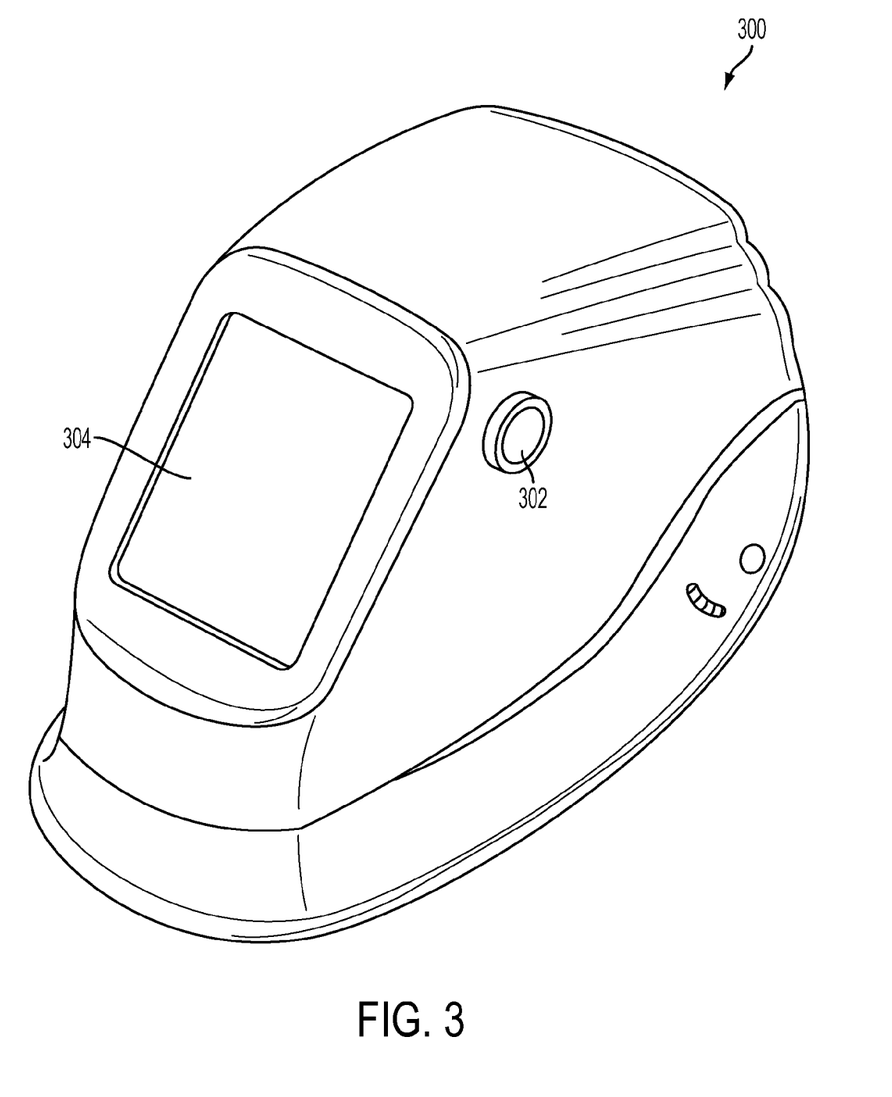
FIG. 3 is an illustration of an auto-darkening welding helmet according to aspects of the present disclosure.

Referring to FIG. 3, an auto-darkening welding helmet 300 according to aspects of the present disclosure includes an external multi-function knob 302 for adjusting the functionality of an auto-darkening lens 304. The auto-darkening lens may include a liquid crystal display (LCD) filter operative to increase or decrease a shading level of the lens in a conventional manner. The knob 302 is located on the outside of a welding helmet 300 within reach of a user while the user is wearing the helmet 300. The multi-function knob 302 functions as a momentary push button switch for selecting a mode defining a lens adjustment parameter to be adjusted and a rotary switch for adjusting levels of the selected parameter according to the selected mode. According to an aspect of the present disclosure, the knob 302 is sized to facilitate gripping for rotation of the knob 302 by a user wearing welding gloves and for actuation of the momentary push button functionality of the knob 302 by a user wearing welding gloves.

Although the term "rotary switch" is used herein, it should be understood that the rotary functionality of the knob 302 may actuate a rotary switch, variable resistor, rotary encoder or any other conventional rotary control input device operable by a rotatable knob 302 whether or not any switching occurs during rotation of the knob 302. For example, the knob 302 may actuate a potentiometer which includes a continuously variable resistor. The term "rotary switch" as used herein is intended to encompass the various conventional rotatable adjustment devices that may include variable resistors, switches, encoders and the like.

Although the push button functionality of the knob 302 is described herein in terms of a momentary switch, it should be understood that other non-momentary types of push button switch functionality may be employed in alternative embodiments to provide a mode selection input by switching between multiple states to cycle between a set of adjustment modes, for example.

Figure 4:
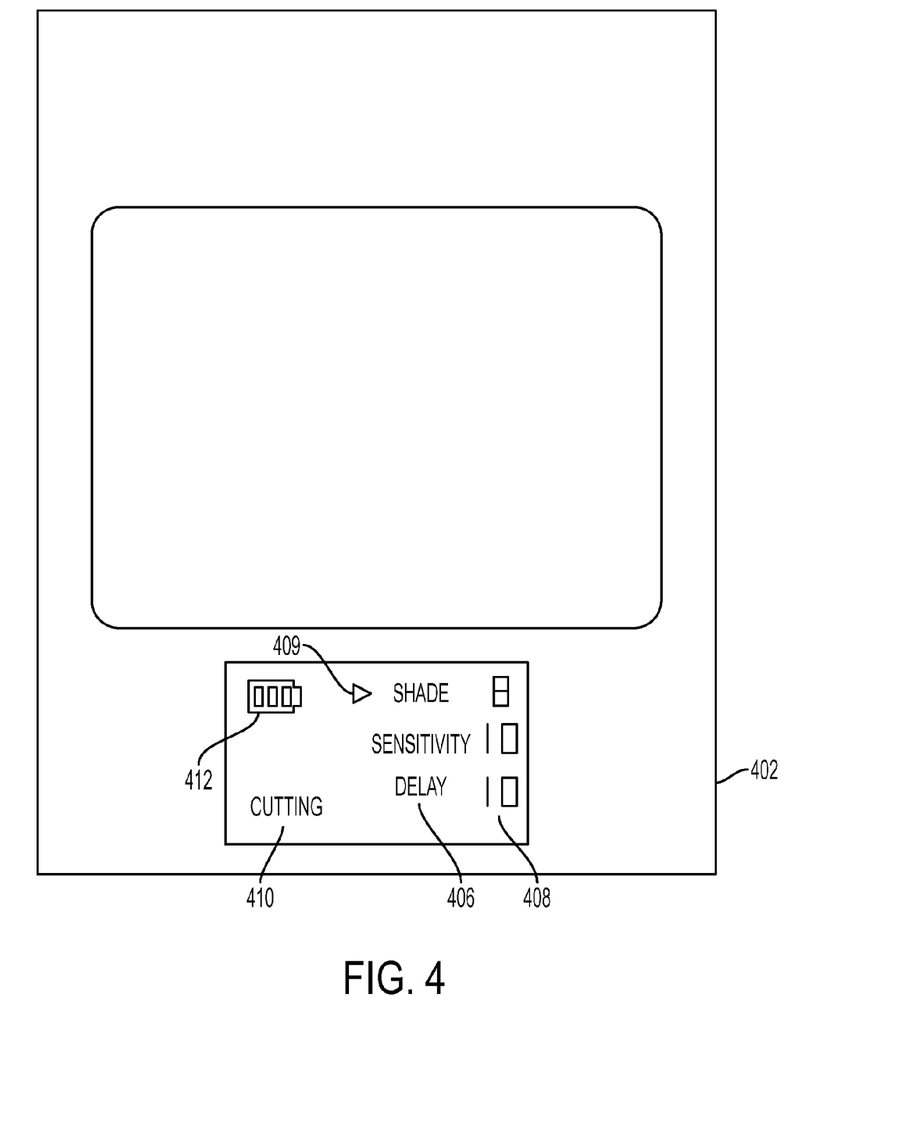
FIG. 4 is an illustration of an internal control status display for an auto-darkening welding helmet according to aspects of the present disclosure.

According to an aspect of the present disclosure the welding helmet 300 includes an internal display of lens control adjustment settings. Referring to FIG. 4, control settings for an auto-darkening welding helmet lens 402 is controlled by the multi-function knob. An internal display 404 indicates the levels of control settings for a set of control parameters for the lens 402. The display 404 may include LCD display elements, light emitting diode (LED) display elements or a combination thereof. According to an aspect of the present disclosure, the display 404 is located within the helmet in a location that is viewable by a user while the user is wearing the welding helmet and while the lens 402 is in a lowered operational state.

The display 404 indicates the setting level 408 of lens control adjustment parameters 406. An adjustment mode indicator 409 indicates which of the parameters 406 is selected for adjustment by actuation of the rotary switch. The parameters 406 include shade, sensitivity, delay and type of welding, for example. According to an aspect of the present disclosure, the setting level 408 of a parameter may be indicated by a numerical level indicator as shown.

Alternatively, a setting level may be indicated by a graphical indication, a color indication or a text indication, for example. In the embodiment shown in FIG. 4, the setting level 408 of a shade parameter, a sensitivity parameter and a delay parameter are displayed as a numerical indicator. The selected type of welding parameter is displayed as a text indicator 410. The internal display 404 may optionally include a battery level indicator 412, according to an aspect of the present disclosure.

Figure 5:
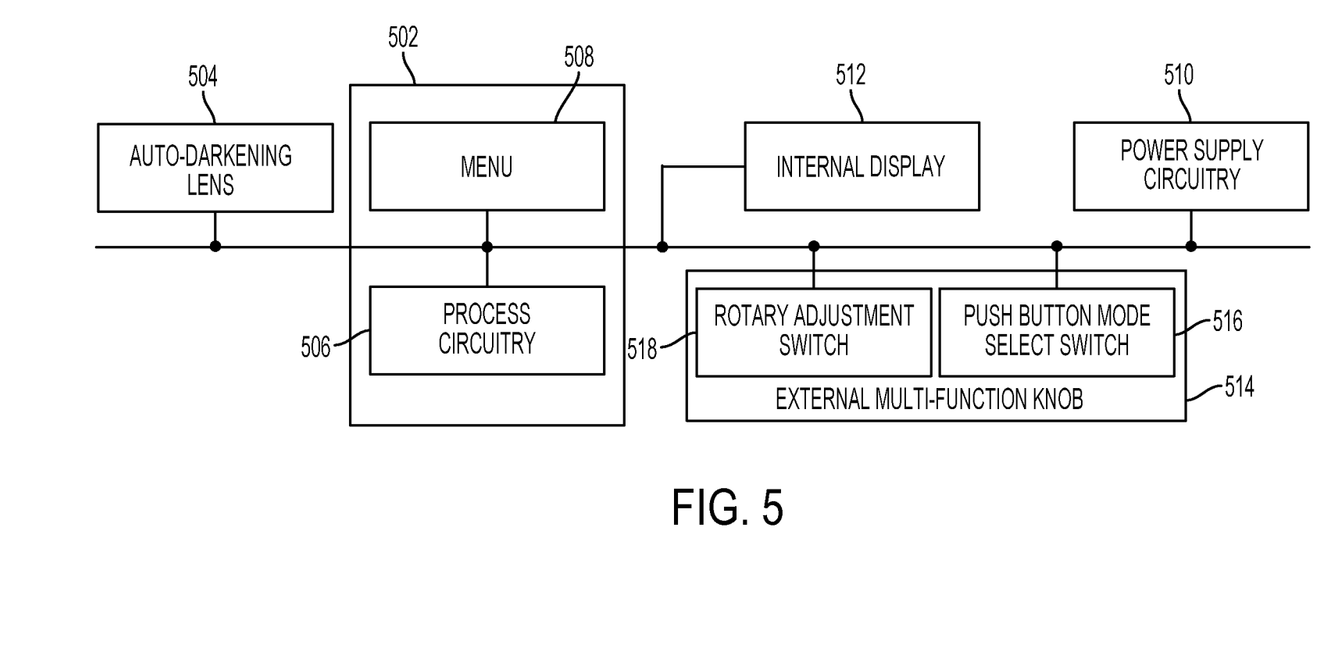
FIG. 5 is a system block diagram illustrating an apparatus for controlling an auto-darkening welding helmet according to aspects of the present disclosure.

Referring to FIG. 5, an example of a welding helmet control circuitry configuration according to an aspect of the present disclosure includes an auto darkening lens 504 coupled to power supply circuitry 510 and control circuitry 502 in a conventional manner. The power supply circuitry 510 includes a power source such as a battery, for example. The control circuitry 502 includes processing circuitry 506 coupled to a memory 502. According to aspects of the present disclosure, the control circuitry 502 is coupled to an internal display 512 and an external multi-function knob 514. The multi-function knob 514 includes a push button mode select switch 516 incorporated with a rotary switch 518 for adjusting a selected lens control parameter. The status of the lens control parameters including real-time feedback of a selected adjustment mode and adjustment settings during manipulation of the multi-function knob 518 is viewable on the internal display 512 by a user while the user is wearing the welding helmet.

Figure 6:
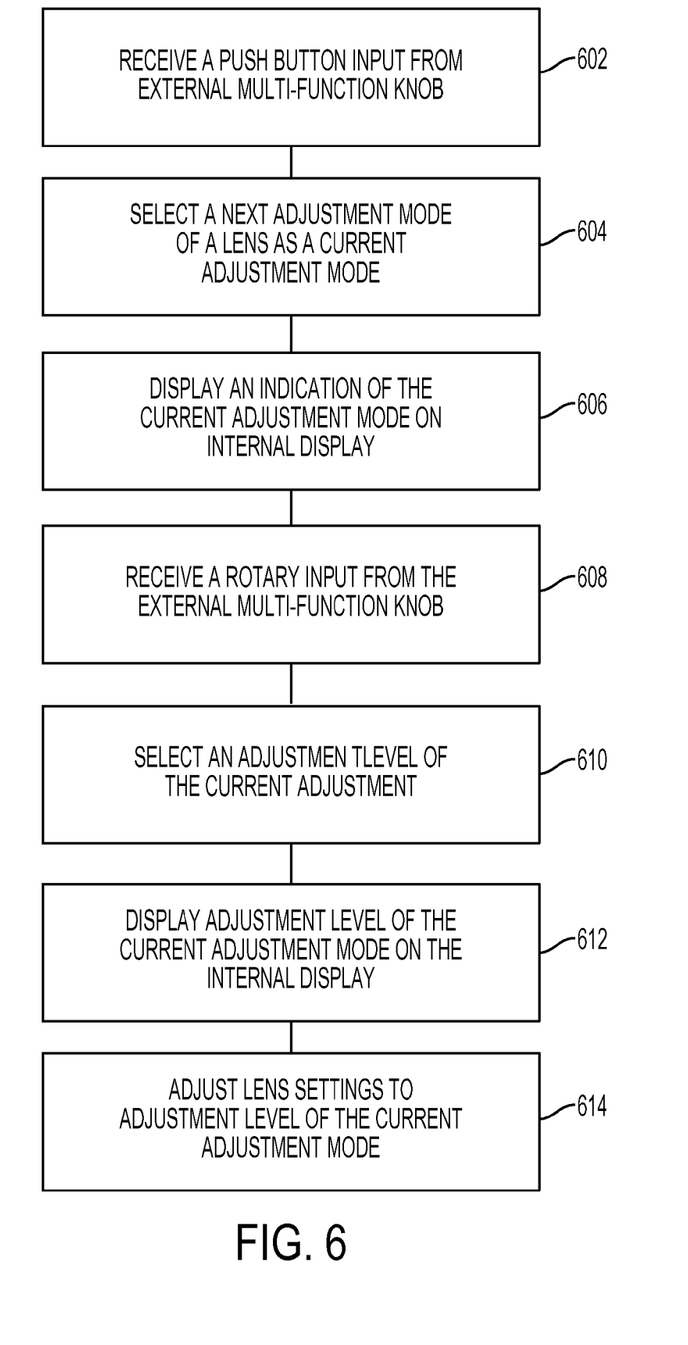
FIG. 6 is process flow diagram illustrating a method for controlling an auto-darkening welding helmet according to aspects of the present disclosure.

A method 600 for controlling an auto-darkening lens according to an aspect of the present disclosure is described with reference to FIG. 6. At block 602, the method includes receiving a push button input from a multi-function knob on an external portion of wearable lens retaining structure such as a welding helmet or welding visor. At block 604, the method includes selecting a next adjustment mode of a lens as a current adjustment mode in response to receiving the push button input. According to an aspect of the present disclosure, the current adjustment mode may include shade, sensitivity, delay and type of welding, for example.

At block 606, the method includes displaying an indication of the current adjustment mode on an internally located display in response to selecting the next adjustment mode. At block 608, the method includes receiving a rotary input from the multi-function knob, at block 610; the method includes selecting an adjustment level of the current adjustment mode in response to receiving the rotary input. At block 612, the method includes displaying an indication of the adjustment level of the current adjustment mode on the internally located display. At block 614, the method includes adjusting settings of the lens to correspond to the adjustment level of the current adjustment mode.

According to aspects of the present disclosure, the method also includes configuring the internally located display to indicate a corresponding current adjustment level for shade, sensitivity and delay settings of the lens in a field of view of a user while the lens is in a lowered operational position. According to another aspect of the present disclosure, the method may also include configuring the internally located display to indicate a currently selected type of welding in the group consisting of cutting, welding, stick, metal inert gas (MIG), aluminum MIG, metal active gas (MAG), flux cored, and tungsten inert gas (TIG), for example.

According to an aspect of the present disclosure, the multi-function knob when pushed is a momentary-on style of operation, which causes the control circuitry to cycle between a set of adjustment modes such as shade, sensitivity, delay and type of welding process. The rotating functionality of the multi-function knob allows adjustment of a parameter level in the selected mode such as level of shade, sensitivity setting, delay time or type of welding.

According to an aspect of the present disclosure, when the lens of the disclosed auto-darkening welding helmet is in a lowered operational position, as would be the position used during welding, a user who is wearing the helmet may view a head-up display of the selected adjustment mode and corresponding setting level. This internal selection mode and level indication combined operation of the external multi-function knob allows a user to make quick and accurate adjustments of all control settings based on the individual conditions during a welding operation without raising the lens, removing the helmet or removing welding gloves.

Although the methods and apparatus disclosed herein are described in terms of a welding helmet implementation, it should be understood that the various aspects of the present disclosure may be implemented in auto-darkening eye protection apparatus that may not necessarily include a full helmet structure. For example, a welding visor may be configured with a multi-function knob on an external surface of a visor frame portion, in which the visor includes a lens control setting display configured within the frame portion as described herein according to aspects of the present disclosure. Thus, the term welding helmet as used here is not limited to structures that shield a user's entire face or head.

As used herein, the term "coupled" or "communicably coupled" can mean any physical, electrical, magnetic, or other connection, either direct or indirect, between two parties. The term "coupled" is not limited to a fixed direct coupling between two entities.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. An eye protection apparatus for use by a user, comprising:
    a wearable lens retaining structure including external and internal surfaces;
    a lens coupled to the wearable lens retaining structure;
    lens control circuitry operably coupled to the lens;
    a rotatable and depressible knob operably coupled to the lens control circuitry and disposed on and extending outwardly from the external surface, wherein depression of the knob causes a first lens setting of the lens to be controlled, and rotation of the knob causes a second lens setting of the lens to be controlled; and
    a display displayable on an internal surface of the lens and operably coupled to the lens control circuitry.

2. The apparatus of claim 1, wherein the knob has a diameter of at least ¾ inch and extends outwardly from the external surface at least ½ inch.

3. The apparatus of claim 1, further comprising a lens control setting displayable in the display in a field of view of the user when the lens is in a closed position.

4. The apparatus of claim 1, further comprising a lens control setting displayable in the display.

5. The apparatus of claim 1, wherein the lens control circuitry is adapted to cause the display to display a status of one of the first and second lens settings in response to the knob being respectively depressed or rotated.

6. The apparatus of claim 1, wherein the lens control circuitry is adapted to:
    select a next adjustment mode of the lens as a current adjustment mode in response to the knob being depressed;
    cause the display to display an indication of the current adjustment mode;
    select an adjustment level of the current adjustment mode in response to the knob being rotated;
    cause the display to display an indication of the adjustment level of the current adjustment mode; and
    adjust the first and second lens settings to correspond to the adjustment level of the current adjustment mode.

7. The apparatus of claim 6, wherein the current adjustment mode includes any one of shade, sensitivity, and delay settings of the lens, and type of welding.

8. The apparatus of claim 7, wherein the display is adapted to display a corresponding current adjustment level for shade, sensitivity, and delay settings of the lens and type of welding.

9. The apparatus of claim 1, wherein the lens control circuitry is adapted to cause the display to indicate a currently selected type of welding including any one of cutting, stick, metal inert gas (MIG), aluminum MIG, metal active gas (MAG), flux cored, and tungsten inert gas (TIG).

* * * * *